United States Patent [19]

Jordan et al.

[11] Patent Number: 5,522,725
[45] Date of Patent: Jun. 4, 1996

[54] METHOD OF ENHANCING THE BOND STRENGTH OF AN ORTHODONTIC APPLIANCE TO A TOOTH

[75] Inventors: Russell A. Jordan, Rancho Cucamonga; James D. Cleary, Glendora, both of Calif.

[73] Assignee: Minnesota Mining and Manufacturing Company, St. Paul, Minn.

[21] Appl. No.: 322,989

[22] Filed: Oct. 14, 1994

[51] Int. Cl.$^6$ .................................................. A61C 7/16
[52] U.S. Cl. .................................................. 433/9; 433/8
[58] Field of Search ................... 433/8, 9, 180, 433/183

[56] References Cited

U.S. PATENT DOCUMENTS

| | | | |
|---|---|---|---|
| D. 290,040 | 5/1987 | Kelly | D24/16 |
| D. 340,523 | 10/1993 | Barngrover | D24/180 |
| 3,765,091 | 10/1973 | Northcutt . | |
| 3,930,311 | 1/1976 | Andrews . | |
| 3,975,824 | 8/1976 | Lee . | |
| 4,068,379 | 1/1978 | Miller et al. . | |
| 4,100,678 | 7/1978 | Yatabe . | |
| 4,165,561 | 8/1979 | Miller et al. . | |
| 4,243,386 | 1/1981 | Kawaguchi | 433/9 |
| 4,322,206 | 3/1982 | Reynolds | 433/9 |
| 4,430,061 | 2/1984 | Webb et al. | 433/9 |
| 4,460,336 | 7/1984 | Smith et al. | 433/9 |
| 4,479,527 | 10/1984 | Boettcher | 164/34 |
| 4,531,566 | 7/1985 | Boettcher | 164/246 |
| 4,544,353 | 10/1985 | Maurer et al. | 433/9 |
| 4,604,057 | 8/1986 | Viglietti | 433/9 |
| 4,626,209 | 12/1986 | Tsai et al. | 433/9 |
| 4,661,059 | 4/1987 | Kanno | 433/9 |
| 4,681,538 | 7/1987 | DeLuca et al. | 433/9 |
| 4,698,017 | 10/1987 | Hanson | 433/11 |
| 4,752,221 | 6/1988 | Hanson et al. | 433/9 |
| 4,838,786 | 6/1989 | Reher et al. | 433/9 |
| 4,842,513 | 6/1989 | Haarmann | 433/9 |
| 4,927,361 | 5/1990 | Smith et al. | 433/9 |
| 4,936,773 | 6/1990 | Kawaguchi | 433/9 |
| 5,071,344 | 12/1991 | Wong et al. | 433/8 |
| 5,108,285 | 4/1992 | Tuneberg | 433/9 |
| 5,154,606 | 10/1992 | Wildman | 433/8 |
| 5,295,823 | 3/1994 | Farzin-Nia | 433/9 |

FOREIGN PATENT DOCUMENTS 2563426  10/1985  France .

OTHER PUBLICATIONS

Supreme™ Mini-Twin brochure, Ortho Organizers, Inc., copyright date unkown.

*Primary Examiner*—Robert P. Swiatek
*Attorney, Agent, or Firm*—Gary L. Griswold; Walter N. Kirn; James D. Christoff

[57] ABSTRACT

Bond strengths of orthodontic appliances are enhanced by applying heat to heat softenable projections of a bonding base of the appliance, and then moving outer portions of the projections in lateral directions to present overhanging regions. The overhanging regions provide undercut areas that mechanically interlock with adhesive when the appliance is bonded to a tooth and the adhesive hardens. The method is useful for plastic appliances as well as other appliances that are made of materials exhibiting thermoplastic characteristics during at least one phase of their manufacture.

10 Claims, 4 Drawing Sheets

METHOD OF ENHANCING THE BOND STRENGTH OF AN ORTHODONTIC APPLIANCE TO A TOOTH

BACKGROUND OF THE INVENTION

1. Field of the Invention

This invention relates to a method of enhancing the bond of an orthodontic appliance that is directly bonded to a tooth surface, and is particularly useful for enhancing the bond of an orthodontic appliance made of a plastic material.

2. Description of the Related Art

Orthodontic treatment concerns movement of malpositioned teeth to orthodontically correct positions. In certain types of orthodontic treatment, tiny, slotted appliances known as brackets are affixed to anterior, bicuspid and cuspid teeth, and other appliances known as buccal tubes are secured to the molar teeth. An orthodontic archwire is placed in the slots of the brackets and is tied in place using small elastomeric O-rings or metallic ligature wires. Ends of the archwire are inserted into channels of the buccal tubes.

As orthodontic treatment progresses, the archwire serves as a track to guide movement of the teeth toward desired positions. Bends, loops or twists are often placed in the archwire to urge movement of the teeth. Alternatively, one or more elastic members secured to brackets or buccal tubes of certain teeth provide a force to move the associated teeth to their correct positions.

In the past, it was common practice to weld each bracket to a metal orthodontic band that was, in turn, placed around the selected tooth in encircling relation and cemented in place. Such bracket and band assemblies provided a strong connection to the underlying tooth but were also highly visible and often an embarrassment to the patient. The use of welded bracket and band assemblies was also troublesome in that teeth vary widely in size and shape and a certain amount of time is typically required to carefully select each band so that the chosen band complementally fits onto the corresponding tooth.

In more recent years and with the development of new adhesives, the use of brackets that are directly bonded to teeth has become increasingly popular. For example, it is now common practice to bond metallic and ceramic brackets directly to the tooth surface. Bonding the bracket to the tooth surface may be carried out by chemical adhesion, or a combination of chemical and mechanical adhesion, and is a function of the type of adhesive used as well as the material of which the bracket is made.

Regardless of the type of adhesive and bracket used, it is important that the bracket is bonded to the tooth with sufficient strength so that the bracket does not spontaneously debond from the tooth under normal conditions as orthodontic treatment progresses. If a bracket does debond from the tooth before treatment is finished, the patient should return to the orthodontist so that the archwire can be removed and a new bracket bonded in its place. Obviously, such a procedure is time consuming and a nuisance both to the orthodontist as well as to the patient.

The manufacturers of orthodontic appliances have directed attention in recent years toward a variety of manufacturing methods for enhancing the mechanical bond between the base of the bracket and the adhesive. Some brackets, for example, are provided with a dimpled surface to increase the surface area of contact between the bracket and the adhesive, such as is shown in U.S. Pat. No. 4,243,386. Others have suggested the use of small particles, roughened surfaces or other means to provide increased surface area, such as described in U.S. Pat. Nos. 4,626,209 and 4,752,221.

A particularly effective method of enhancing the mechanical bond strength of a directly bonded orthodontic appliance is by providing a bonding base for the appliance with overhanging portions, so that one or more undercut regions are attained. When such an appliance is bonded to a tooth surface, the adhesive flows into the undercut regions and hardens, establishing a mechanical interlock between the adhesive and the bonding base.

Metal brackets sold by 3M Unitek Corporation under the trademark "DYNA-LOK" are made in a machining operation, and during machining a series of slots are made in the base. Edges of the slots are subsequently deformed by a knurling process such that the slots present undercut channels. A drawing of one type of "DYNA-LOK" brand bracket is shown in U.S. Design Pat. No. 290,040.

Other metal brackets, such as 3M Unitek's miniature twin brackets, are manufactured using a metal injection molding process. A mold assembly has cavities that provide upstanding pegs or projections on the base of the bracket. The brackets are tumbled during a finishing operation in a tumbling mill using a media that peens over the outer edges of the projections. An example of such peened-over projections is shown in, for example, U.S. Design Pat. No. 340,523.

Other methods for providing undercut regions include the use of a porous wire mesh that is fixed to the bracket base, such as is illustrated in U.S. Pat. No. 4,068,379. In addition, U.S. Pat. No. 4,110,678 describes the use of a sandblasting and oxidizing solution to provide undercut pores in the base of metal brackets.

Another method for making orthodontic appliances with a bonding base having undercut regions is described in U.S. Pat. No. 5,393,486. The method described in this reference involves in one embodiment the use of a plastic mesh that is embedded in the base of the bracket during a molding operation, and is subsequently degraded by heat, solvent or other process to establish a witness impression of undercut regions.

Many attempts have been made over the years to use orthodontic brackets made of plastic materials rather than metal because brackets made of plastic material are often less visible in the oral cavity and hence more aesthetic than brackets made of metal. However, conventional plastic brackets are often considered unsatisfactory because chemical adhesion of plastic brackets directly to the teeth is often not sufficiently strong to prevent premature, spontaneous debonding of the bracket when certain conventional adhesives are used. Moreover, the machining and/or tumbling processes described above in connection with metal brackets for facilitating a mechanical interlock are not generally satisfactory for one reason or another when attempted for plastic brackets.

As can be appreciated, there is a continuing need in the art for new efficient and effective methods of manufacturing plastic brackets and for enhancing the bond of plastic brackets to teeth. Preferably, such methods would also be useful when used in connection with appliances made of other materials that exhibit thermoplastic characteristics during at least one phase of manufacture.

SUMMARY OF THE INVENTION

The present invention is directed to a method of enhancing the bond strength of an orthodontic appliance to a tooth, and comprises the step of providing an orthodontic appliance body that is made of a heat softenable material and the step of applying heat to one or more projections of a bonding base of the body in order to soften an outer portion of the projections and move the projections in one or more lateral directions. The method also includes the step of cooling the projections once the projections have moved sufficiently to present one or more overhanging regions that are wider in a lateral direction than the width of underlying portions of the respective projection.

As can be appreciated, each overhanging region presents an undercut for receiving adhesive that, once hardened, mechanically interlocks the appliance to the adhesive. The use of heat to soften and move portions of the projections is relatively inexpensive and can be quickly accomplished, unlike other processes that are significantly more time consuming. The method is advantageous for enhancing the bond of plastic orthodontic appliances as well as appliances made of other materials such as unsintered, "green" metal injection molding preforms that exhibit thermoplastic characteristics.

DETAILED DESCRIPTION OF THE PREFERRED EMBODIMENT

Figure 1:
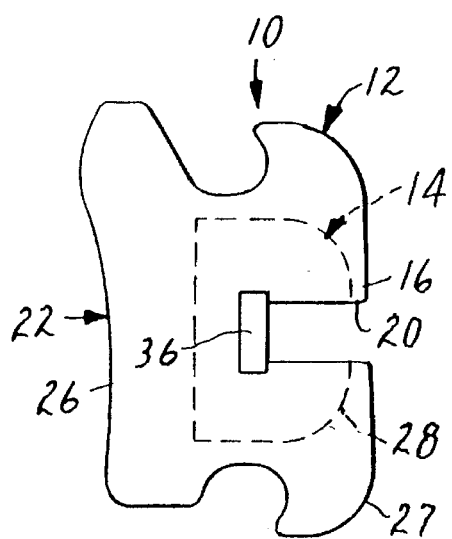
FIG. 1 is an end elevational view of an orthodontic appliance constructed in accordance with the present invention.
Figure 2:
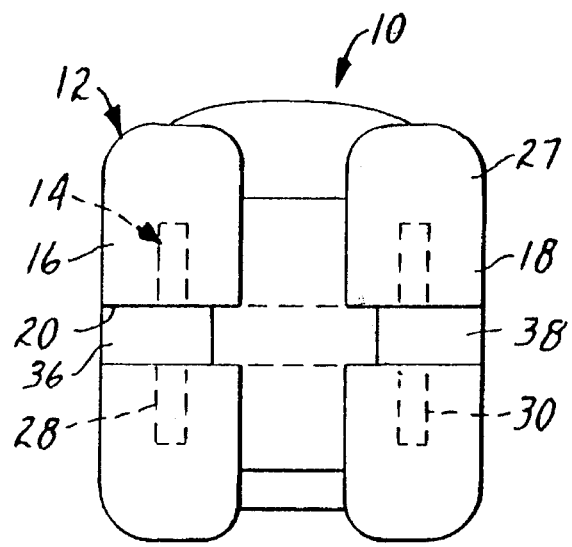
FIG. 2 is a front view looking toward a buccolabial side (i.e., toward a lip or cheek facing side) of the appliance illustrated in FIG. 1.
Figure 3:
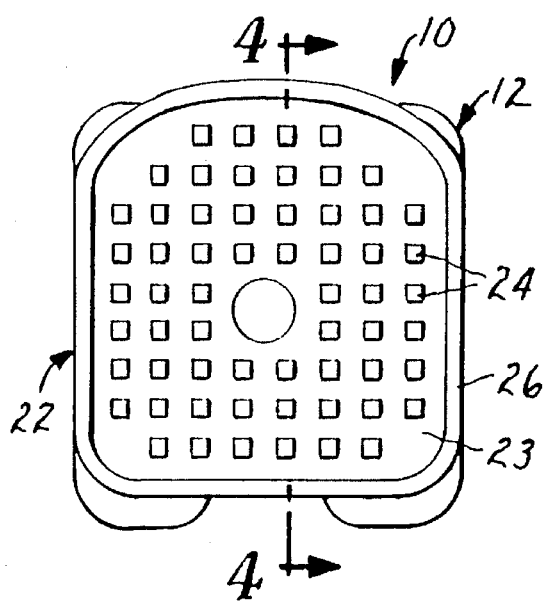
FIG. 3 is a rear view looking toward a lingual or tooth facing side of the appliance illustrated in FIGS. 1 and 2, and wherein a bonding base of the appliance is illustrated during an intermediate step of manufacture.

An orthodontic appliance 10 constructed in accordance with the principles of the present invention is illustrated in FIGS. 1–5 and is broadly designated by the numeral 10. The appliance 10 that is shown in the drawings for exemplary purposes is an orthodontic bracket, although the invention is equally applicable to other orthodontic appliances such as buccal tubes or bands that are directly bonded to a tooth surface.

In more detail, the appliance 10 includes a plastic body 12 and a metallic framework 14 that is partially embedded in the plastic body 12. The body 12 has a mesial (i.e., in a direction toward the center of the patient's dental arch) tiewing section 16 and a distal (i.e., in a direction away from the center of the patient's dental arch) tiewing section 18.

An elongated archwire slot 20 extends through the sections 16, 18 in a mesial-distal direction. Each of the tiewing sections 16, 18 include an occlusal tiewing (i.e., the tiewing next to the outer tip of the tooth) and a gingival tiewing (i.e., the tiewing next to the patient's gingiva or gums). The occlusal and gingival tiewings are located on opposite sides of the archwire slot 20.

The body 12 includes a bonding base 22 with a lingual surface 23 that faces the tooth to be bonded. The bonding base surface has a contour and optionally a compound contour that closely matches the contour of the portion of the tooth surface that receives the appliance 10.

The bonding base 22 includes a number of spaced apart pegs or projections 24 that comprise a first projection set of one or more projections and that are arranged in a grid-like array. Each projection 24 extends lingually away from the surface 23 and includes a shank preferably having side walls parallel to mesial, distal, occlusal and gingival sides of the appliance 10. The shank of each projection 24 is slightly larger in cross-sectional area at its base (i.e., next to the surface 23) relative to its outer, lingual end for facilitating removal of the appliance 10 from the mold.

Figure 4:
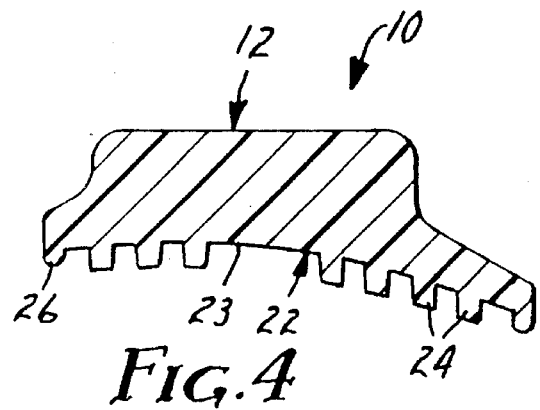
FIG. 4 is an enlarged partial cross-sectional view taken along lines 4—4 of FIG. 3.

A second projection set comprising one or more projections includes a rim 26 that extends around the periphery of the bonding base 22 and surrounds the projections 24. As illustrated in FIG. 4, the rim 26 initially has a height in a lingual direction (as measured from the surface 23) that is less than the lingual height of the projections 24. Preferably, the height of each projection 24 in a lingual direction is identical such that the outer edges of the projections 24 lie in a curved reference plane that is identical in contour but slightly spaced from a curved bonding base surface 23.

The body 12 is made of a heat softenable, thermoplastic material. Preferred materials include polycarbonate containing glass fibers (such as no. DF-1004 resin from LNP) and unfilled polycarbonate (such as "LEXAN" brand, No. HP1; from GE).

Preferably, the body 12 has an outer, buccolabial surface 27 that is relatively rough in surface texture in comparison to conventional plastic brackets, in order to enable the body 12 to present a pleasing, translucent appearance. The rough outer surface 27 is especially advantageous when the body 12 is made of an unfilled plastic such as polycarbonate that might otherwise present a transparent appearance. The rough outer surface 27 diminishes specular reflection such as is sometimes observed in connection with transparent plastic brackets.

The rough outer surface 27 diffuses light passing through the body 12 and effectively masks the framework 14 from view. Further, the translucent appearance of the body 12 matches the translucent appearance presented by translucent polycrystalline ceramic brackets (such as "TRANSCEND" brand brackets from 3M Unitek). As a result, the appliance 10 may be used interchangeably with such ceramic brackets without undue noticeable differences in appearance.

The outer surface 27 has a surface roughness of greater than 43 microinches $R_A$ (arithmetic mean roughness), and more preferably a surface roughness of greater than about 50 microinches $R_A$. The rough outer surface 27 may be made by directing a stream of abrasive material (such as 150 micrometer alumina grit using a MICROBLASTER brand sandblaster) toward the buccolabial surface 27 of the body 12. Alternatively, the surfaces of the forming tooling for making the body 12 are roughened in such a fashion that the buccolabial surface of the body 12 once molded has a similar roughened characteristic.

Figure 5:
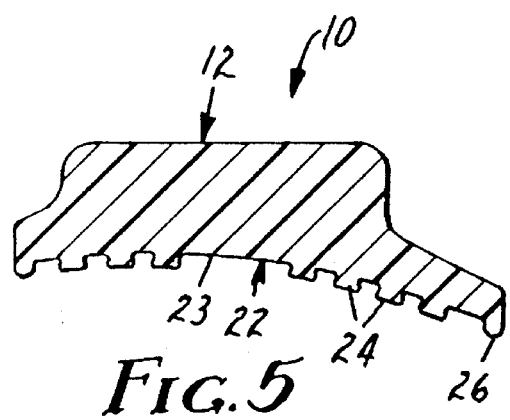
FIG. 5 is a view somewhat similar to FIG. 4 except that projections of the bonding base have been deformed to provide a mechanical interlock with orthodontic adhesive.

The bond strength of the appliance 10 is enhanced by deforming the projections 24 in lateral directions to provide overhanging regions. The projections 24 are deformed by applying heat to an outer portion of the projections 24 to soften the outer portions and move the outer portions in lateral directions (i.e., laterally of a central, labiolingual reference axis of each projection 24). When the body is made of polycarbonate, heat is applied to the outer portion of the projections 24 until the temperature of the outer portions is above the glass transition temperature of polycarbonate. As the outer portions are softened and moved, the projections 24 change from the peg-shaped appearance illustrated in FIG. 4 to the flattened knob-like or mushroom cap appearance that is illustrated in FIG. 5.

Once deformed, the projections 24 each present an overhanging region that is wider in lateral direction (i.e., in directions perpendicular to the aforementioned labiolingual reference axis) than the width of underlying portions of the shank of the respective projection 24. Each overhang presents an undercut that is adapted to receive orthodontic adhesive when the appliance 10 is bonded to the tooth. Once the adhesive has hardened, the adhesive together with the overhanging portions of the projections 24 establish an interlocking, structural connection that has significant strength and is suitable for the forces normally encountered in orthodontic treatment.

Preferably, the appliance 10 is pretreated by applying a pretreating solution comprising i) a polymerizable component, ii) a solvent capable of at least partially solubilizing the plastic dental appliance, and iii) a photoinitiator system to the bonding base 22; and curing the pretreating solution by exposure to actinic radiation. Components i) and ii) may be the same or different materials. A conventional adhesive (such as "CONCISE" brand or "TRANSBOND XT" brand adhesive from 3M Unitek) can then be used to bond the appliance 10 to the selected tooth. Optionally, the appliance 10 may additionally be precoated with an orthodontic adhesive and packaged accordingly.

The polymerizable component optionally may be selected from any materials suitable for use as dental adhesive resins that will alone or in combination with other materials act to at least partially solubilize the plastic dental appliance. Examples of such materials are acrylates and methacrylates, such as C 1–6 alkyl acrylates and methacrylates and C 1–12 alkoxyalkyl acrylates and methacrylates, and more preferably C 1–2 alkyl acrylates and methacrylates and C 1–4 alkoxyalkyl acrylates and methacrylates. Other preferred polymerizable components are monomers traditionally used in dental materials, such as the dimethacrylate derived from the reaction between methacrylic acid and the diglycidyl ether of bisphenol A ("Bis-GMA"), tetraethylene glycol dimethacrylate, Bisphenol A diethyleneglycol dimethacrylate ("BisEMA") and triethylene glycol dimethacrylate ("TEDGMA"). Polymers, such as polymethyl methacrylate, may also be incorporated in the pretreatment compositions as appropriate.

Figure 7:
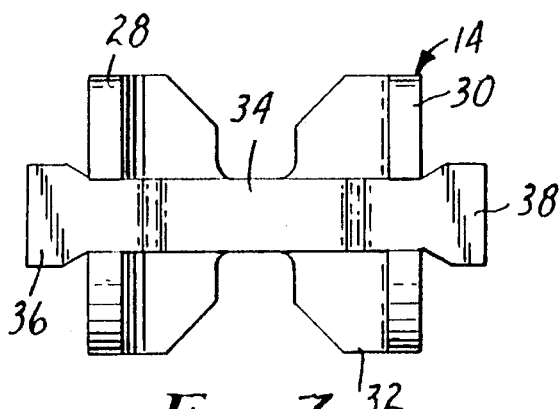
FIG. 7 is a plan view looking toward a buccolabial side of the framework shown in FIG. 6.
Figure 6:
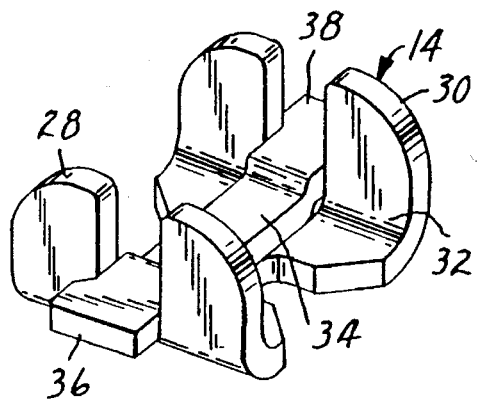
FIG. 6 is a perspective view of a framework of the appliance depicted in FIGS. 1–5.
Figure 8:
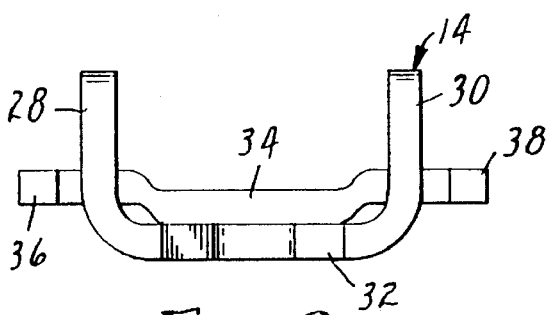
FIG. 8 is a side view of the framework shown in FIGS. 6–7.

The framework 14 has a generally H-shaped configuration, and is shown alone in FIGS. 6–8. The framework 14 is optionally coated or otherwise colored by ink or paint (such as an epoxy paint), porcelain or other material to match the color of the tooth or the color of the plastic material. The coating may be applied by a wet or a dry electrostatic coating process.

The framework 14 includes a mesial portion 28 that extends in the mesial tiewing section 16 in a transverse direction with respect to the longitudinal axis of the archwire slot 20. The framework 14 also includes a distal portion 30 that extends in the distal tiewing section 18 in a transverse direction with respect to the longitudinal axis of the archwire slot. "Transverse", as used herein, means ninety degrees plus or minus twenty degrees, as angles other than perpendicular may be useful for "angulated" brackets. Preferably, however, the framework 14 has a shape and size similar to that shown in the drawings so that a single framework can be used with a variety of both angulated as well as non-angulated brackets.

The mesial portion 28 and the distal portion 30 each include an occlusally-facing edge that is coplanar with a gingival side of the archwire slot 20. The portions 28, 30 also each include a gingivally-facing edge that is coplanar with an occlusal side of the archwire slot 20.

In the particular embodiment shown in FIGS. 6–8, the framework 14 is made of two initially separate pieces: a first, generally "U"-shaped piece 32 having opposed, parallel legs that present the mesial and distal portions 28, 30, and a second piece 34 that is connected to the first piece 32 and extends through channels of the first piece 32. The first piece 32 is connected to the second piece 34 by use of an interference fit in areas where the second piece 34 extends through channels of the first piece 32. Optionally, the first piece 32 and second piece 34 are connected together by spot welding or by brazing.

The second piece 34 includes a first end portion 36 that is located mesially of the mesial portion 28 and a second end portion 38 that is located distally of the distal portion 30. Each of the end portions 36, 38 have a buccolabially-facing surface that is located on and coplanar with a lingual side of the archwire slot 20. The end portions 36, 38 provide bearing surfaces for the archwire when received in the archwire slot 20. The end portions 36, 38 are especially advantageous in providing control of rotation of the associated tooth when attempts are made to rotate the tooth about its long axis.

As illustrated in FIGS. 6–8, each of the end portions 36, 38 has an occlusally-extending section and a gingivally-extending section that extends beyond occlusal and gingival sides respectively of the portion of the archwire slot 20 that is defined by the plastic body 12. Such sections are embedded within the body 12 and help anchor the framework 14 and particularly the second piece 34 in the body 12 so that the second piece 34 does not separate from the first piece 32 or the body 12 under normal, expected conditions. An intermediate portion of the second piece 34, located between the mesial portion 28 and the distal portion 30, is not preferably exposed and instead is covered by a portion of the body 12, such that a buccolabially-facing surface of such intermediate portion is spaced in a lingual direction from the lingual side of the archwire slot 20.

Figure 9:
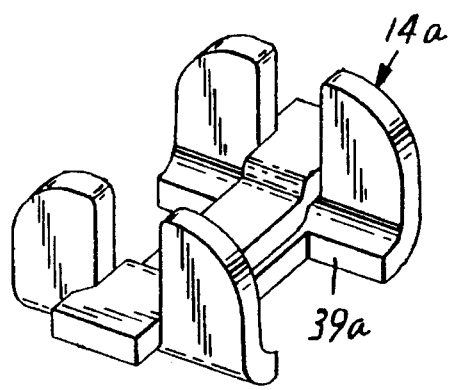
FIG. 9 is a perspective view of a framework according to an alternate construction for the appliance shown in FIGS. 1–5.

An alternate framework 14a is illustrated in FIG. 9, and is substantially the same as the framework 14 described above in connection with FIGS. 6–8. However, a first piece 32a of the framework 14a has an intermediate section with a U-shaped notch 39a that is greater than the corresponding notch formed in the intermediate portion of the first piece 32 of framework 14, in order to reduce the visibility of the framework 14 and improve aesthetics of the appliance 10 in instances where the body 12 is made of a transparent or translucent material.

Figure 11:
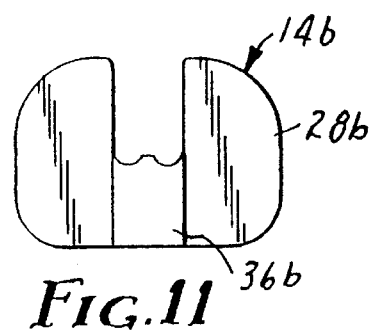
FIG. 11 is an end view of the framework shown in FIG. 10.
Figure 10:
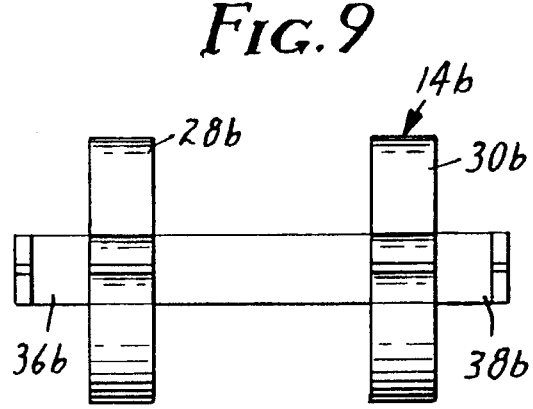
FIG. 10 is a front view looking toward a buccolabial side of a framework according to yet another construction for the appliance illustrated in FIGS. 1–5.
Figure 12:
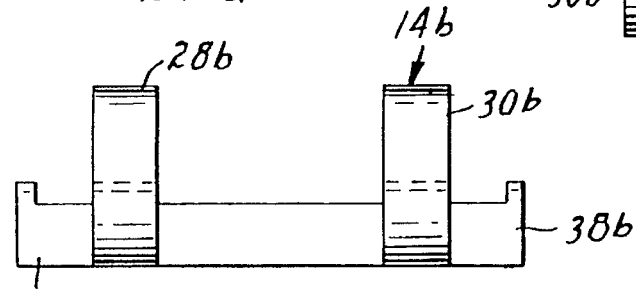
FIG. 12 is a side view of the framework depicted in FIGS. 10–11.

Another alternative framework 14b is illustrated in FIGS. 10–12. The framework 14b is preferably an integral, one-piece construction made by a metal injection molding process, by machining, or by extrusion or cold drawn forming followed by machining.

The framework 14b has a mesial portion 28b, a distal portion 30b and end portions 36b, 38b. The end portions 36b, 38b have a buccolabially-facing edge with a platform that is raised in a buccolabial direction on a lingual side of the archwire slot for engagement with the archwire. Each buccolabial edge has a pair of lingually-extending recesses disposed on opposite, occlusal and gingival sides of the platform, so that only a portion of the end portions 36b, 38b are in contact with the archwire. Moreover, each platform is spaced from the respective mesial and distal portions 28b, 30b by a connector portion that is embedded in the plastic body.

The mesial and distal portions 28b, 30b also each have a raised, buccolabially-facing platform that is located on the lingual side of the archwire slot. The portions 28b, 38b have lingually-extending recesses located on opposite sides of the platform. The platforms and recesses of the end portions 36b, 38b and the mesial and distal portions 28b, 30b have identical double-"U"-shaped configurations when viewed along the length of the archwire slot as shown in FIG. 11, although other configurations are also possible.

Figure 13:
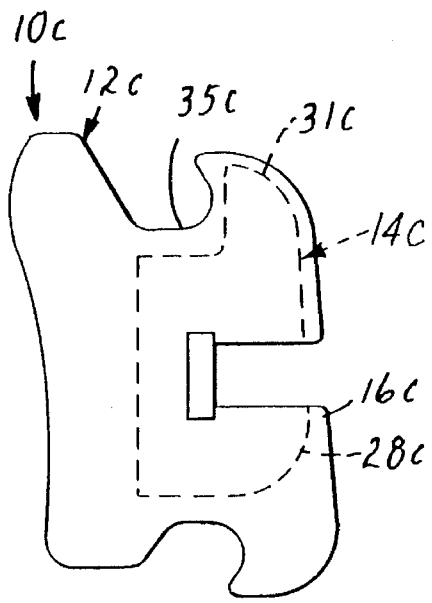
FIG. 13 is an end elevational view of an orthodontic appliance with yet another framework.
Figure 14:
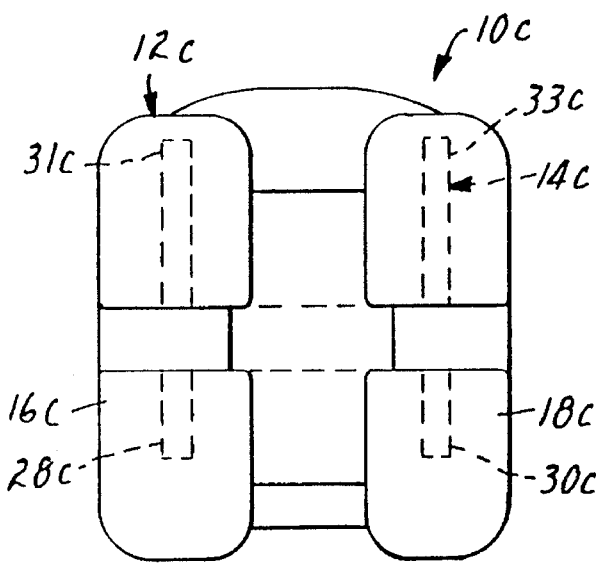
FIG. 14 is a front view looking toward a buccolabial side of the appliance illustrated in FIG. 13.

The framework 14c of an appliance 10c that is depicted in FIGS. 13–14 is somewhat similar to the framework 14 shown in FIGS. 6–8. However, a mesial portion 28c and a distal portion 30c of the framework 14c have sections 31c, 33c respectively that extend into occlusal regions of mesial and distal tiewing sections 16c, 18c of the appliance 10c. Both sections 31c, 33c extend occlusally of an occlusal tiewing undercut 35c that is shaped to receive an archwire ligature.

The sections 31c, 33c effectively prevent undue wear of the tiewing sections 16c, 18c in instances where the patient's opposing dentition frequently contacts the appliance 10c. In such instances, the portion of the body 12c initially covering the sections 31c, 33c may wear away, but the sections 31c, 33c will resist wear and enable the tiewing sections 16c, 18c to serve their intended functions.

Figure 15:
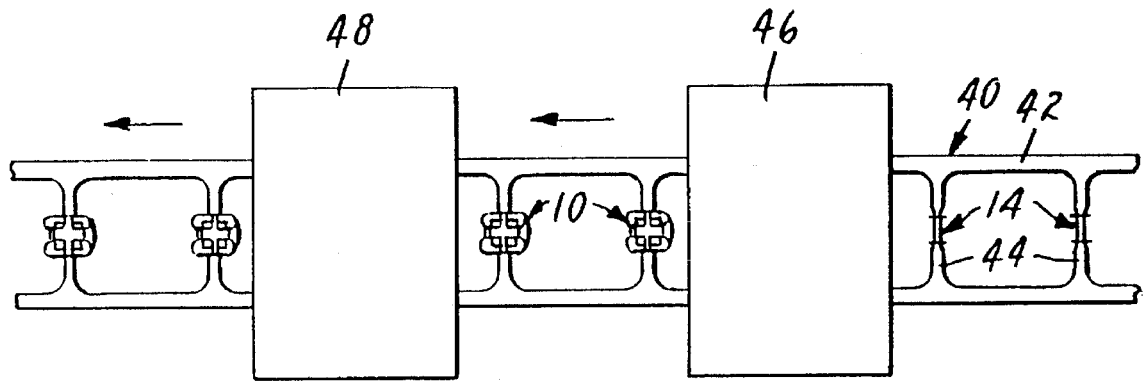
FIG. 15 is a reduced, bottom view in partially schematic form of method steps for making an appliance in accordance with the present invention.

FIG. 15 illustrates a method of making orthodontic appliances such as the appliance 10 in accordance with the invention. As shown, a "ladder"-shaped metal carrier or lattice 40 is provided and includes two side members 42 that are coupled together at a number of spaced apart intervals by a number of connecting members 44. The lattice 40 is made by a metal stamping process using a 0.01 inch (0.25 mm) thick sheet of type 17–4 PH stainless steel. Other possible materials include type 301 stainless steel, a stainless steel that is hardenable by heat treatment, or a cold-worked austenitic material.

Each of the connecting members 44 includes a middle portion that provides part or all of a framework, such as second piece 34 of the framework 14. Each first piece 32 is assembled to a second piece 34. The lattice 40 is advanced from a feed roll to body forming tooling 46, such as a die for injection molding plastic brackets.

In the tooling 46, a quantity of molding material to make the appliance body 12 is placed about the assembled framework 14. In the case of plastic bracket molding, the pressure and temperature within the forming tooling 46 are raised to levels sufficient to injection mold the appliance body 12. After solidification and opening of the tooling 46, the lattice 40 is incrementally advanced in order to bring each appliance 10 to a bonding base projection forming tooling 48. In the tooling 48, a heated mandrel 50 is moved toward the bonding base 22 of each approaching appliance 10 in order to soften outer portions of the projections 24 and move the projections 24 in lateral directions to present overhanging regions.

Figure 17:
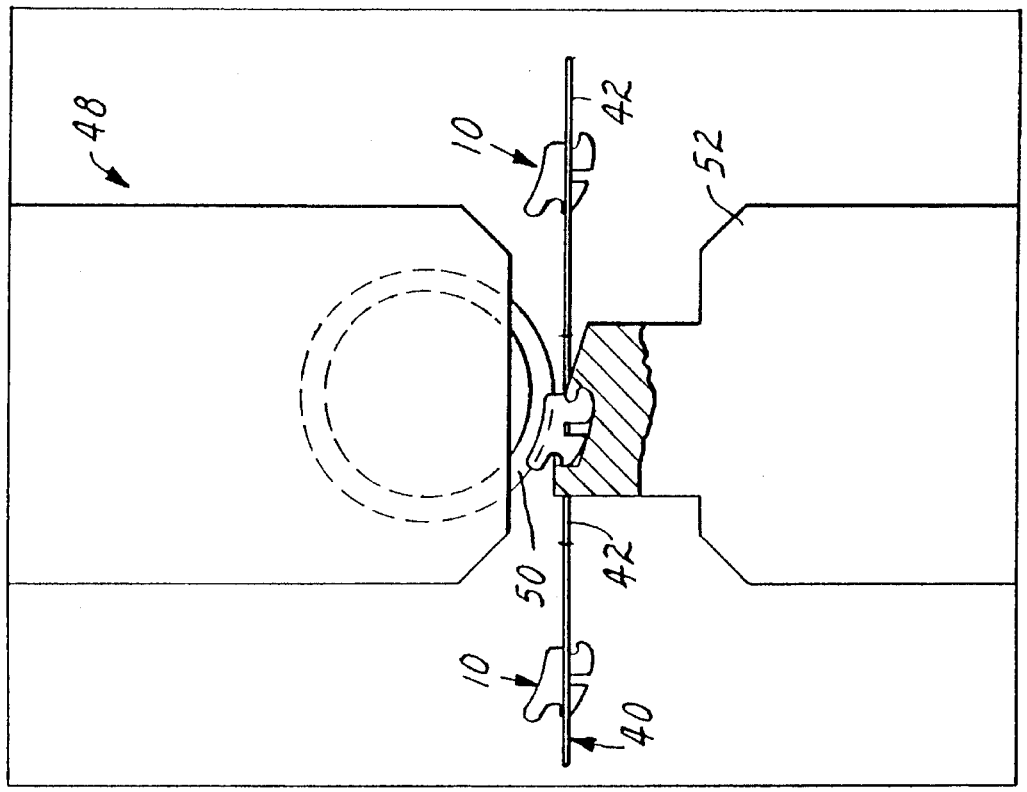
FIG. 17 is a view somewhat similar to FIG. 16 except that a bracket support and a mandrel have engaged one of the appliances on opposite sides in order to carry out the projection forming step.
Figure 16:
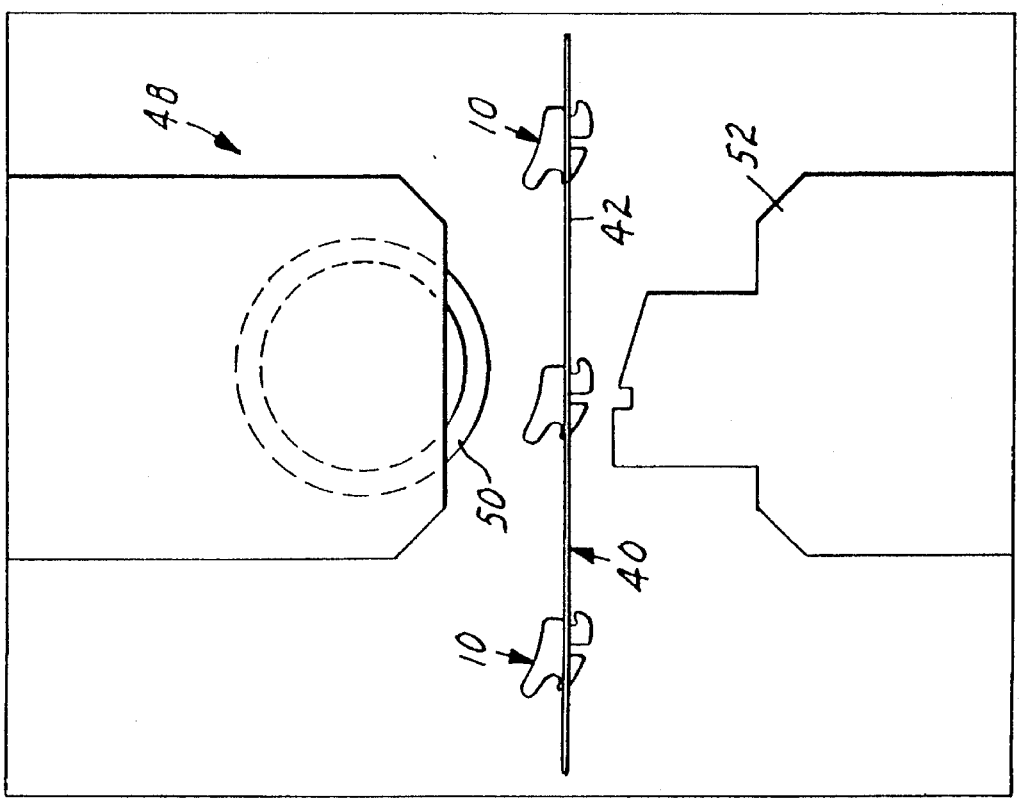
FIG. 16 is a fragmentary, side elevational view of one of the steps of the method shown in FIG. 15 that is preliminary to a projection forming step.

FIGS. 16–17 include additional details of the projection forming tooling 48. The mandrel 50 has a compound curved convex surface that matches the shape of the tooth to which the appliance 10 is to be bonded, and that also matches a curved reference plane that lies across the outer end of each undeformed projection 24 as illustrated in FIG. 4. Preferably, rim 26 has a uniform height such that the outer, lingual edge of the rim 26 is spaced from such reference plane in FIG. 4 an equal distance along the entire extent of the rim 26.

The buccolabial side of the appliance 10 is supported by a support 52 that rises to contact the appliance 10 as the mandrel 50 descends. The support 52 includes a nest that is shaped to complementally receive the appliance 10. Optionally, the support 52 may include movable arms that also engage the appliance 10 to keep it steady during deforming of the projections 24.

As the mandrel 50 advances toward the body 12, the mandrel 50 contacts and deforms the outer portion of each projection 24 until such outer portions take on the configuration as illustrated in FIG. 5. As soon as the mandrel 50 contacts the rim 26, however, further advancement of the mandrel 50 is interrupted and the mandrel 50 is then withdrawn in an opposite direction to enable the projections 24 to cool and harden. The rim 26 serves as a precise stop for advancement of the mandrel 50.

Optionally, the convex head of the mandrel 50 that contacts the appliance 10 is substantially larger in surface area than the area of the bonding base 22, and is mounted on a holder that enables different regions of the head to be used for forming the bonding base 22. In this manner, if one region is worn, the head can be adjusted to bring another region into use.

Referring again to FIG. 15, the lattice 40 is again incrementally advanced once the projections 24 of the bonding base 22 have been deformed in the forming tooling 48 to establish the overhanging regions. The lattice 40 is then wound about a windup roll, or advanced to other processing operations such as a sandblasting operation for roughening the outer surface 27.

Preferably, the connecting member 44 includes two lines of weakness that are located within the body 12 and immediately adjacent the mesial side of the mesial section 16 and the distal side of the distal section 18 after the body 12 is formed. The appliance 10 is separated from the lattice 40 by bending the exposed portions of the connecting member 44. Advantageously, the member 44 fractures along the lines of weakness such that the fractured edges are located inwardly of the sections 16, 18.

EXAMPLE 1

Test sample parts were injection molded in a simulated bracket mold using 20% glass filled polycarbonate (no. DF-1004; from LNP). The sample parts were in the shape of a small, slotted block without tiewing detail and with a flat base having projections.

A projection forming tool was fabricated from a movable weld head ("Thin Line" brand; from Unitek Equipment, Inc.). The weld head had a vertically movable force control member that was movable by an air cylinder and was operable to apply a compressive force through an adjustable coil spring. A block containing a cartridge heater and a thermocouple was connected to the movable force control member of the weld head. The heater and thermocouple were connected to a controller to enable selection and maintenance of a constant temperature.

The block connected to the movable force control member was also coupled to a mandrel having a flat surface. An adjustable timer was also provided. Whenever the force control member was lowered toward a sample part, the force control member actuated a switch that initiated the adjustable timer. At the end of the timed cycle, the force control member was released and retracted upwardly.

The timing cycle was set to 1.5 seconds and the weld head force adjustment was set to a value of "4" which is approximately equal to 8 lbs. (3.6 kg) of force exerted by the moving force control member on the base projections of the sample parts. The controller was set to provide a surface temperature on the mandrel of 300° F. (150° C.). The sample parts were placed on a flat surface beneath the heated mandrel, and the force control member of the weld head was activated.

When the mandrel contacted the sample parts, the projections deformed and spread in lateral directions. A rim of the sample parts surrounding the projections provided an effective stop for the mandrel so that complete collapse of the projections was prevented. The mandrel was raised and the sample part was examined. The projections presented a number of overhanging regions that provided an undercut area suitable for mechanical interlock with bonding adhesive.

EXAMPLE 2

Standard edgewise lateral orthodontic brackets were molded using 20% glass filled polycarbonate (no. DF-1004; from LNP). The brackets were molded with bonding base projections and a rim surrounding the projections. The projections of some of the brackets were deformed by hand using a curved, heated mandrel to establish overhanging regions and corresponding undercuts.

The bond strengths of brackets with projections were compared to brackets having undeformed projections. Five brackets having undeformed projections and five brackets having deformed projections were mounted on metal test rings using a chemical-cure orthodontic adhesive ("CONCISE" brand adhesive; from 3M Unitek). In addition, five brackets having deformed projections and five brackets having undeformed projections were bonded to metal rings using a light-cure orthodontic adhesive ("TRANSBOND" brand adhesive; from 3M Unitek).

Bond strengths were measured using an "INSTRON" brand universal testing machine. For the bond strength test, a wire was placed around either both of the gingival or both of the occlusal tiewings of the bracket and a pulling force was exerted on the wire in a direction perpendicular to a reference line extending between the bracket and the metal ring, such that the brackets were debonded in shear/peel mode. The bonding base of the debonded samples were sputter coated with a mixture of gold and palladium and were examined under a scanning electron microscope.

The mean bond strength was 12.4 lbs. (5.6 kg) and 11.2 lbs. (5.0 kg) for the samples with undeformed projections bonded using light-cure adhesive and chemical-cure adhesive respectively. The mean bond strengths for the samples with deformed projections was 24.5 lbs. (11.1 kg) and 21.5 lbs. (9.8 kg) for the sample parts bonded with light-cure adhesive and chemical-cure adhesive, respectively. The data show that the sample parts having deformed projections exhibited greatly enhanced mean bond strengths that were approximately twice the mean bond strengths of the sample parts with undeformed projections.

Inspection of photographs from the scanning electron microscope revealed significant differences between the sample parts having deformed projections and the sample parts having undeformed projections. The projections of the sample parts subjected to the projection forming tooling had flattened "mushroom" shapes, and fractured pieces of adhesive were retained in the undercut regions of the debonded sample parts. No such retention was observed by examination of the sample parts having undeformed projections.

EXAMPLE 3

Plastic orthodontic brackets of the invention were pretreated by preparing a solution made by mixing three parts of methyl methacrylate (MMA) and one part of BisGMA together until homogeneous. 0.375% camphorquinone (CPQ) and 1% ethyl-4-dimethyl-amino benzoate (EDMAB) were dissolved in the resin mixture. The bonding bases of the plastic brackets (20% glass filled polycarbonate; LNP DF1004) were prepared by application of approximately 2.5 microliters of solution to each bracket. The brackets were allowed to dry for 2 to 3 minutes and then cured by exposure to an "ORTHOLUX XT" brand curing light for 10 seconds. The brackets were stored in air and intermittent exposure to fluorescent light and then tested for bond strength using procedures set out in Example 2 with the following adhesives.

| Adhesive | # of Brackets | Bond Strength lbs/bkt Average | S.D. |
| --- | --- | --- | --- |
| Concise orthodontic bonding adhesive | 15 | 37 | 6.6 |
| Transbond XT Adhesive | 15 | 30 | 8.3 |

Although the preferred embodiments of our invention have been described above in detail, it should be apparent to those skilled in the art that many variations and modifications are possible. For example, the projections could be deformed by moving the brackets toward the mandrel instead of vice versa, or by simply applying heat by flame, laser, etc., without the use of a mandrel. Accordingly, the scope of the invention should not be deemed limited to the embodiments described above, but only by a fair reading of the claims that follow along with their equivalents.

We claim:

1. A method of enhancing the bond strength of an orthodontic appliance to a tooth comprising the steps of:
   providing an orthodontic appliance body that is made of a heat-softenable material;
   applying heat to one or more projections of a bonding base of the body in order to soften an outer portion of the one or more projections and move the outer portion of the one or more projections in one or more lateral directions; and
   cooling the one or more projections once the one or more projections have moved sufficiently to present one or more overhanging regions that are wider in a lateral direction than the width of underlying portions of the respective projection.

2. The method of claim 1, wherein said step of applying heat to one or more projections includes the step of moving a heated mandrel toward the body to contact the one or more projections.

3. The method of claim 2, wherein said step of providing a body made of heat-softenable material includes the step of providing the body with a first projection set comprising one or more projections initially having a certain height and a second projection set comprising one or more projections initially having a height less than said certain height.

4. The method of claim 3, wherein said step of moving a heated mandrel toward the body includes the steps of first contacting at least one projection of the first set, and subsequently contacting at least one projection of the second set.

5. The method of claim 4, including the step of interrupting movement of the mandrel toward the body once the mandrel has contacted one or more projections of the second set.

6. The method of claim 5, wherein the second set comprises a rim surrounding the first set.

7. The method of claim 2, wherein said step of moving a heated mandrel toward the body includes the step of contacting a perimeter rim at least partially surrounding the one or more projections after the mandrel has contacted the one or more projections.

8. The method of claim 7, including the step of interrupting movement of the mandrel toward the body once the mandrel has contacted the rim.

9. The method of claim 2, wherein said step of moving a heated mandrel is carried out using a platen with a mandrel having a curved surface that is similar in curvature to the tooth to which the appliance is to be bonded.

10. The method of claim 1, wherein said step of applying heat to one or more projections includes the step of raising the outer portion of the one or more projections to a temperature above the glass transition temperature of the heat-softenable material.

* * * * *